United States Patent [19]

Onsager

[11] Patent Number: 4,731,386

[45] Date of Patent: Mar. 15, 1988

[54] PROCESS FOR THE PREPARATION OF METHANOL IN LIQUID PHASE

[75] Inventor: Olav-T. Onsager, Trondheim, Norway

[73] Assignee: Sintef, Trondheim - NTH, Norway

[21] Appl. No.: 891,184

[22] PCT Filed: Oct. 17, 1985

[86] PCT No.: PCT/NO85/00067

§ 371 Date: Jul. 22, 1986

§ 102(e) Date: Jul. 22, 1986

[87] PCT Pub. No.: WO86/03190

PCT Pub. Date: Jun. 5, 1986

[30] Foreign Application Priority Data

Nov. 23, 1984 [NO] Norway ................................. 844675

[51] Int. Cl.$^4$ ............................................. C07C 27/06
[52] U.S. Cl. ..................................... 518/700; 502/156
[58] Field of Search .......................................... 518/700

[56] References Cited

U.S. PATENT DOCUMENTS 4,567,204 1/1986 Mednick ............................ 518/700

FOREIGN PATENT DOCUMENTS

| 1175768 | 10/1984 | Canada. | |
|---|---|---|---|
| 809803 | 8/1951 | Fed. Rep. of Germany | 518/700 |
| 57-128642 | 8/1982 | Japan | 518/700 |
| WO84/00360 | 2/1984 | PCT Int'l Appl. | 518/700 |

*Primary Examiner*—Howard T. Mars
*Attorney, Agent, or Firm*—Wenderoth, Lind & Ponack

[57] ABSTRACT

A process for preparing methanol in a liquid reaction medium by reaction of carbon monoxide and hydrogen in the presence of a catalyst system consisting of an alkali metal alcoholate and a copper catalyst, wherein the liquid reaction medium in the reactor in addition to methanol and methyl formate contains at least 50% by volume of a non-polar organic solvent having a dielectricity constant which is lower than that of pure methanol at the same temperature.

7 Claims, No Drawings

PROCESS FOR THE PREPARATION OF METHANOL IN LIQUID PHASE

This invention relates to the use of specific organic solvents in the catalytic preparation of methanol from carbon monoxide and hydrogen. A mixture of an alkali metal alcoholate and a heterogeneous copper catalyst is used as catalyst. The formation of methanol ($CH_3OH$) takes place by reaction of the gases carbon monoxide (CO) and hydrogen ($H_2$) which are dissolved in the liquid reaction mixture, according to the following reaction:

$$CO + 2H_2 \rightarrow CH_3OH$$

As will be known the industrial production of methanol today takes place almost solely by bringing synthesis gas (CO, $CO_2$ and $H_2$) to reaction over a heterogeneous copper catalyst at a temperature in the range: 200°–270° C. and a pressure in the range: 50–150 bar. In European Patent Application No. 81300344.9 there is described a catalytic preparation of methanol in the presence of an organic solvent in order to obtain a better temperature control in the process. However, the catalysts used are solid and no alkali metal alcoholate is present.

According to German Patent Specification No. 809803 and Norwegian Patent Application No. 81.2279 it is known to prepare methanol in a liquid reaction mixture by reacting CO and $H_2$ in the presence of catalyst systems consisting of an alkali or alkaline earth metal alcoholate and a hetergeneous copper catalyst. In both the above processes methanol has been preferred as the solvent for the reaction, although others have been mentioned without further illustration, and no particular solvent effects have been described. From the literature it is also known that the catalytic activity of alkali metal alcoholates in general may be substantially increased by means of additions which solvatize the cation such as cyclic polyethers and polyethyleneglycol dimethylethers or by using polar organic solvents such as dimethylformamide and dimethylsulfoxide. (See Ugelstad, J. and Rokstad, O.A. Acta Chemica Scandinavia 18 (1964), 474 and Ugelstad, J., Jenssen, B. and Mork, P.C. Acta Chemica Scandinavia 16 (1962) 323).

The subject matter of the application is characterized by the features given in claim 1.

Thus, according to the present invention it has surprisingly been found that the presence of non-polar organic solvents having weak cation solvatizing properties, in a liquid phase which otherwise consists of methanol and methylformate, to a substantial extent increases the catalytic activity of catalyst systems consisting of an alkali metal alcoholate and a heterogeneous copper catalyst for the reaction of CO and $H_2$ to methanol.

In order to obtain an essential improvement of reaction rate and selectivity at least 50% (by volume) of the liquid phase must be inert organic solvents which have a lower dielectric constant (polarity) than that of methanol. Information regarding the polarity and dielectric constant of organic substances is given in standard handbooks such as Handbook of Chemistry and Physics 57th Ed. (1976-1977) CRC-Press, Cleveland, Ohio 44128, page E-55 to E-58. According to this reference methanol has a dielectric constant of 32.62 at 25° C. Thus, according to the invention all inert organic solvents which have a lower dielectric constant than 32.62 at 25° C. may be used. Typical examples of such solvents are aliphatic and cycloaliphatic hydrocarbons such as n-hexane, n-decane, cyclohexane and decalin, aromatic compounds such as benzene, toluene, ethylbenzene, xylene and diphenyl, ethers such as diethylether, dibutylether and 1,4 dioxane, esters such as ethylformate, propylformate, butylformate, octylformate, ethylacetate and methylstearate, and alcohols such as ethanol, propanol, n-butanol, iso-butanol, 2-methyl-2-propanol, pentanol, hexanol, 2-ethylhexanol and 1-decanol etc. Such solvents having lower polarity than that of methanol have herein also been designated as "non-polar".

A combination of an alkali metal alcoholate and a copper catalyst is used as catalyst for the process according to the invention. Typical alkali metal alcoholates are lithium methoxide, sodium methoxide, potassium methoxide, rubidium methoxide, cesium methoxide, sodium ethoxide, sodium butoxide and analogeous compounds. As copper catalyst may be mentioned pure copper metal (i.e. Raney copper), but advantageously there may be used a copper catalyst which in addition to copper also contains other elements such as chromium, zinc, aluminium, zirconium, titanium, nickel, cobalt, iron, manganese, barium, lithium, sodium, potassium and oxygen. Most suitably a copper catalyst of the copper chromite type is used.

The reaction of synthesis gas to methanol takes place at a temperature below 240° C. and a pressure below 100 bar. Most suitably a temperature in the range 70°–150° C., particularly 90°–130° C., and a pressure in the range 5–60 bar is chosen. The composition of the synthesis gas may be chosen within wide limits with respect to the ratio between CO and $H_2$. Most suitably a molar ratio between CO and $H_2$ within the limits $CO/H_2 = \frac{1}{8}$ to 1/1 is chosen.

The reaction of synthesis gas to methanol may be carried out discontinuously or continously by using known reactor types for the reaction of gas to products in a liquid reaction mixture. In addition to methanol minor amounts of methyl formate are formed as byproduct. The products may be removed from the reactor in the form of gases or in liquid form. Methyl formate may be separated from methanol by a simple distillation according to known technique and is recovered as a byproduct or is recirculated to the reactor. By recirculating methylformate to the reactor an improved selectivity to methanol is obtained.

Methanol is an important chemical intermediate which today i.a. is used for the production of formaldehyde and methylesters of different carboxylic acids. In the future it is expected that methanol and methanol-derivatives will play an important part as energy carriers and octane number raising additives to petrol.

The following examples will illustrate the invention further.

EXAMPLE 1

(a) Preparation of copper catalyst

Copper ammonium chromate, $Cu(OH)NH_4CrO_4$, was prepared by Adkin's method by adding a solution of copper nitrate to a solution of ammonium dichromate in water and at the same time adjusting the pH of the solvent to fall within the range 5.8 to 6.0 by addition of ammonia. The precipitate was filtered from the mixture and washed with water. Then the product was dried at 105° C. for 16 hours, crushed to a fine powder and then dried for 20 hours at the same temperature. In order to obtain an active copper catalyst the copper ammonium chromate was thermally decomposed in an inert nitrogen atmosphere at 305° C. for two hours according to the process described in Norwegian Patent Application No. 81.2279 and prereduced in an acid resistant steel autoclave as a slurry in methanol for 2 hours at 170° C. and 80 bar hydrogen pressure. After the prereduction the copper chromite catalyst was washed 3 times with methanol to remove water from the mixture and dried in vacuum of about 1-2 mm Hg.

(b) Reaction of synthesis gas to methanol 2.0 g of copper catalyst prepared according to the above process, 50 cm$^3$ of methanol and 20 m Mol of sodium methoxide were charged to a 100 cm$^3$ acid resistant steel autoclave (SS 316) equipped with magnetic stirrer, temperature and pressure control means and inlets for synthesis gas to the gas phase above the catalyst mixture.

The intial reaction rate ($r_o$) for the formation of methanol and the selectivity to methanol after a reaction time of one hour based on reacted amount of synthesis gas (CO/H$_2$=½) were determined at a reaction temperature of 90° C. and a pressure of 35 bar. The result from this experiment has been given under experiment number 1 in the following table I.

A series of analogous experiments were then carried out with the difference that instead of pure methanol the mixtures of methanol and organic solvent given in experiments 2-10, table I were used. The results from these experiments have also been included in table I.

TABLE I

| Experiment No. | Test results Liquid phase composition % (Volume) | $r_o$ | selectivity to methanol % |
|---|---|---|---|
| 1 | 100 methanol | 81 | 61 |
| 2 | 75 methanol 25 cyclohexane | 94 | 73 |
| 3 | 47 methanol 53 cyclohexane | 104 | 83 |
| 4 | 15 methanol 85 cyclohexane | 156 | 94 |
| 5 | 5 methanol 95 cyclohexane | 120 | 96 |
| 6 | 15 methanol 85 decalin | 160 | 94 |
| 7 | 15 methanol 85 1,4 dioxane | 196 | 95 |
| 8 | 15 methanol 85 p-xylene | 170 | 95 |
| 9 | 20 methanol 80 n-butyl-stearate | 150 | 92 |
| 10 | 15 methanol 85 toluene | 183 | 93 |

$r_o$: g(methanol) · (dm$^3$)$^{-1}$ · h$^{-1}$

In addition to methanol methyl formate is formed as byproduct. The selectivity to methanol has been calculated in such a manner that also the methanol used for the formation of methyl formate has been included.

The results illustrate that the use of non-polar organic solvents, particularly in amounts above 50% of the liquid phase, to an essential extent increases the activity of the catalyst system.

Control experiments with the polar solvents dimethyl formamide and dimethylsulfoxide which have a higher dielectricity constant than that of methanol, and solvents which are characterized by cation solvatizing properties such as tetraethylene glycol dimethylether, illustrated that such systems resulted in a lower catalytic activity than that which was obtained in pure methanol at otherwise identical test conditions.

EXAMPLE 2

The same experimental procedure as described in Example 1 was used. However, the reaction of synthesis gas (CO/H$_2$=½) to methanol was carried out at a higher temperature (110° C.) and in the presence of a higher amount of catalyst (3.0 g copper catalyst and 62.5 m Mol NaOCH$_3$). The results from this experiment are shown in Table II.

TABLE II

| Experiment No. | Test results Liquid phase composition % (Volume) | $r_o$ | Selectivity to methanol % |
|---|---|---|---|
| 11 | 15 methanol 85 1,4 dioxane | 1125 | 99 |

$r_o$: g(methanol) · (dm$^3$)$^{-1}$h$^{-1}$

Compared with the results given in Table 1 Experiment No. 11 illustrates that the rate of formation of methanol in the presence of an organic solvent increases with increasing reaction temperature and increasing amounts of catalyst, so that very high rates of formation of the desired product may be obtained at moderate synthesis gas pressures (35 bar).

EXAMPLE 3

The same experimental procedure as described in Example 1(b) was used. Instead of the copper catalyst prepared by ourselves, a commercial copper chromite catalyst of the type G-89 (Girdler-Südchemie Katalysator GmbH, München, West-Germany) of the following nominal composition was used: 39% Cu, 32% Cr and 2.5% Mn (Rest oxygen) and 60 m Moles of lithium ethoxide (LiOC$_2$H$_5$) as alcoholate catalyst. The other reaction conditions were as follows: temperature: 110° C. and synthesis gas (CO/H$_2$=½) pressure: 60 bar. Compared with the methanol formation rate obtained in this system by using pure methanol as liquid reaction medium an approximately double rate was obtained by using a liquid reaction medium consisting of 85 volume % of decalin and 15 volume % of methanol at the start of the experiment.

EXAMPLE 4

The same experimental procedure as described in Example 1 was used. The reaction of synthesis gas (CO/H$_2$=½) to methanol/methyl formate was carried out at a temperature of 110° C. and a pressure of 86 bar. As catalyst 25 m Moles of methyl alcoholate (CH$_3$O$^-$) in the form of Na OCH$_3$ or Ba(OCH$_3$)$_2$ respectively and 2.0 g copper catalyst were used. The effect of increasing amounts of decalin as solvent in a mixture with methanol was investigated in the two systems. The results with respect to the initial formation rate of methanol and methylformate ($r_o$) based on the activity of the Cu catalyst, has been illustrated in Tables III (the NaOCH$_3$ system) and IV (the Ba(OCH$_3$)$_2$ system).

TABLE III

| the NaOCH$_3$ system | |
|---|---|
| Liquid phase composition % (Volume) | $r_o$ (g product) (g Cu-cat.)$^{-1}$h$^{-1}$ |
| 100 methanol | 16.2 |

TABLE III-continued the NaOCH₃ system

| Liquid phase composition % (Volume) | $r_o$ (g product) (g Cu-cat.)$^{-1}$h$^{-1}$ |
|---|---|
| 80 methanol + 20 decalin | 16.8 |
| 60 methanol + 40 decalin | 17.4 |
| 40 methanol + 60 decalin | 19.2 |
| 20 methanol + 80 decalin | 27.0 |

TABLE IV the Ba(OCH₃)₂ system

| Liquid phase composition % (Volume) | $r_o$ (g product) (g Cu-cat.)$^{-1}$h$^{-1}$ |
|---|---|
| 100 methanol | 13.5 |
| 80 methanol + 20 decalin | 11.1 |
| 60 methanol + 40 decalin | 8.7 |
| 40 methanol + 60 decalin | 6.3 |
| 20 methanol + 80 decalin | 3.9 |

The results given in Table III and Table IV illustrate that the reaction rate in the sodium methoxide system increases with increasing additions of decalin as solvent, while the reaction rate in the analogous barium methoxide system decreases under the same conditions.

EXAMPLE 5

Experiment No. 11 in Example 2 was carried out in the presence of methane so that the partial pressure of methane in the reactor was 6 bar, and the total gas pressure in the reactor was 41 bar (35 bar synthesis gas +6 bar methan). The initial rate of formation of methanol in the system ($r_o$) was found to be 1146 g of methanol per dm³ reaction mixture per hour, and the selectivity to methanol was 99%.

This experiment illustrates that very high reaction rates may be obtained by using gas mixtures consisting of methane and synthesis gas in the process.

I claim:

1. Process for preparing methanol in a liquid reaction medium by reaction of carbon monoxide and hydrogen in the presence of a catalyst system consisting of an alkali metal alcoholate and copper chromite, wherein the liquid reaction medium in the reactor, in addition to methanol and methyl formate, contains at least 50% by volume of a non-polar organic solvent having a dielectric constant which is lower than that of pure methanol at the same temperature.

2. Process according to claim 1, wherein a reaction medium is used which, in addition to methanol and methyl formate, contains decalin.

3. Process according to claim 1, wherein characterized by using a reaction medium is used which in addition to methanol and methyl formate, contains p-xylene.

4. Process according to claim 1, wherein a reaction medium is used which in addition to methanol and methyl formate, contains dioxane.

5. Process according to claim 1, wherein a reaction medium is used which, in addition to methanol and methyl formate, contains p-butyl stearate.

6. Process according to claim 1, wherein a reaction medium is used which in addition to methanol and methyl formate, contains cyclohexane.

7. Process according to claim 1, wherein a reaction medium is used which in addition to methanol and methyl formate, contains toluene.

* * * * *